United States Patent
Wu et al.

(10) Patent No.: US 9,004,070 B2
(45) Date of Patent: Apr. 14, 2015

(54) TRACHEOTOMY TUBE SET

(76) Inventors: Mao-Tsun Wu, Taichung (TW); Chen Yang, Guishan Township, Taoyuan County (TW); Yen-Ni Hung, Taipei (TW); Hui-Ping Liu, Taipei (TW)

( * ) Notice: Subject to any disclaimer, the term of this patent is extended or adjusted under 35 U.S.C. 154(b) by 398 days.

(21) Appl. No.: 13/540,646

(22) Filed: Jul. 3, 2012

(65) Prior Publication Data
US 2014/0007882 A1 Jan. 9, 2014

(51) Int. Cl.
*A61M 16/00* (2006.01)
*A61M 16/04* (2006.01)

(52) U.S. Cl.
CPC ....... *A61M 16/0465* (2013.01); *A61M 16/0488* (2013.01); *A61M 2202/0208* (2013.01); *A61M 16/0445* (2014.02)

(58) Field of Classification Search
USPC .................... 128/200.24, 200.26, 207.14–18; 23/17.12; 604/96, 101.01, 101.05, 103, 604/103.03, 103.05–103.09, 104–106
See application file for complete search history.

(56) References Cited

U.S. PATENT DOCUMENTS

| | | | | | |
|---|---|---|---|---|---|
| 2,854,983 | A | * | 10/1958 | Baskin | 604/103.11 |
| 4,018,231 | A | * | 4/1977 | Wallace | 128/207.15 |
| 4,921,478 | A | * | 5/1990 | Solano et al. | 604/509 |
| 5,112,347 | A | * | 5/1992 | Taheri | 606/200 |
| 5,176,693 | A | * | 1/1993 | Pannek, Jr. | 606/159 |
| 6,251,109 | B1 | * | 6/2001 | Hassett et al. | 606/45 |
| 6,623,451 | B2 | * | 9/2003 | Vigil | 604/99.01 |
| 2006/0184192 | A1 | * | 8/2006 | Markworth et al. | 606/198 |

* cited by examiner

*Primary Examiner* — Rachel Young
*Assistant Examiner* — Joseph R Conte, III

(57) ABSTRACT

A tracheotomy tube set is provided with a tracheotomy tube including: a cannula including a connecting member at a proximal end and a bellows member joining to the connecting member, a balloon cuff formed proximal to a distal end of the cannula, a first wing extending from one side of one end of the balloon cuff, a second wing extending from the other side of one end of the balloon cuff, a first wedge balloon formed between the first wing and an insertion section between the balloon cuff and the distal end of the cannula, an opposite second wedge balloon formed between the second wing and the insertion section, and a line having one end communicating with both the first and second wedge balloons; and a fixation device including a split flange, a hole through the split flange, and two slots formed at both sides of the fixation device respectively.

6 Claims, 5 Drawing Sheets

TRACHEOTOMY TUBE SET

BACKGROUND OF THE INVENTION

1. Field of the Invention

The invention relates to tracheotomy tubes and, more particularly, to a tracheotomy tube set having a cannula adapted to insert into the trachea during tracheotomy, so that air inflated first and second wedge balloons may pivotably push first and second wings outward until being fastened at joining portions of the primary bronchi and the trachea for preventing tracheomalacia from occurring.

2. Description of Related Art

Tracheotomy consists of making an incision on the anterior aspect of the neck and opening a direct airway through an incision in the trachea. The resulting stoma can serve independently as an airway or as a site for a tracheotomy tube to be inserted. The tracheotomy tube provides a secured airway for an ill patient or for those in need of mechanical ventilators.

A balloon cuff is an important part of the tracheotomy tube. A balloon cuff is required to be inflated. However, a balloon cuff inflated for a long time may cause tracheomalacia, i.e., a condition characterized by flaccidity of the tracheal support cartilage which leads to tracheal collapse especially when increased airflow is demanded. These processes are exaggerated in tracheomalacia, leading to airway collapse on expiration.

For alleviating such a condition, the balloon cuff is required to be fully inflated. However, it can cause the trachea to be flaccid after periods of time. Moreover, the fully inflated balloon cuff cannot solve air leakage. A Binova tube is devised to solve the leakage by passing around the flaccid trachea (i.e., the balloon cuff is disposed farther away from the trachea). However, replacement of the more flaccid trachea with another Binova tube having a greater diameter is the only undesired solution.

Thus, the need for improvement still exists.

SUMMARY OF THE INVENTION

It is therefore one object of the invention to provide a tracheotomy tube set comprising: a hollow tracheotomy tube comprising a cannula including a connecting member at a proximal end and a bellows member joining to the connecting member, a balloon cuff formed just proximal to a distal end of the cannula, a first wing extending from one side of one end of the balloon cuff, a second wing extending from the other side of one end of the balloon cuff, a first wedge balloon formed between the first wing and an insertion section between the balloon cuff and the distal end of the cannula, a second wedge balloon, opposite to the first wedge balloon, formed between the second wing and the insertion section, and a line having one end communicating with both the first and second wedge balloons; and a fixation device comprising a split flange, a hole through the split flange, and two slots formed at both sides of the fixation device respectively. The cannula is inserted into the trachea during a tracheotomy. Air is pumped into both the first and second wedge balloons for inflation from the line, and the inflated first and second wedge balloons pivotably push the first and second wings outward until fastened at joining portions of the primary bronchi and the trachea.

The above and other objects, features and advantages of the invention will become apparent from the following detailed description taken with the accompanying drawings.

DETAILED DESCRIPTION OF THE INVENTION

Figure 1:
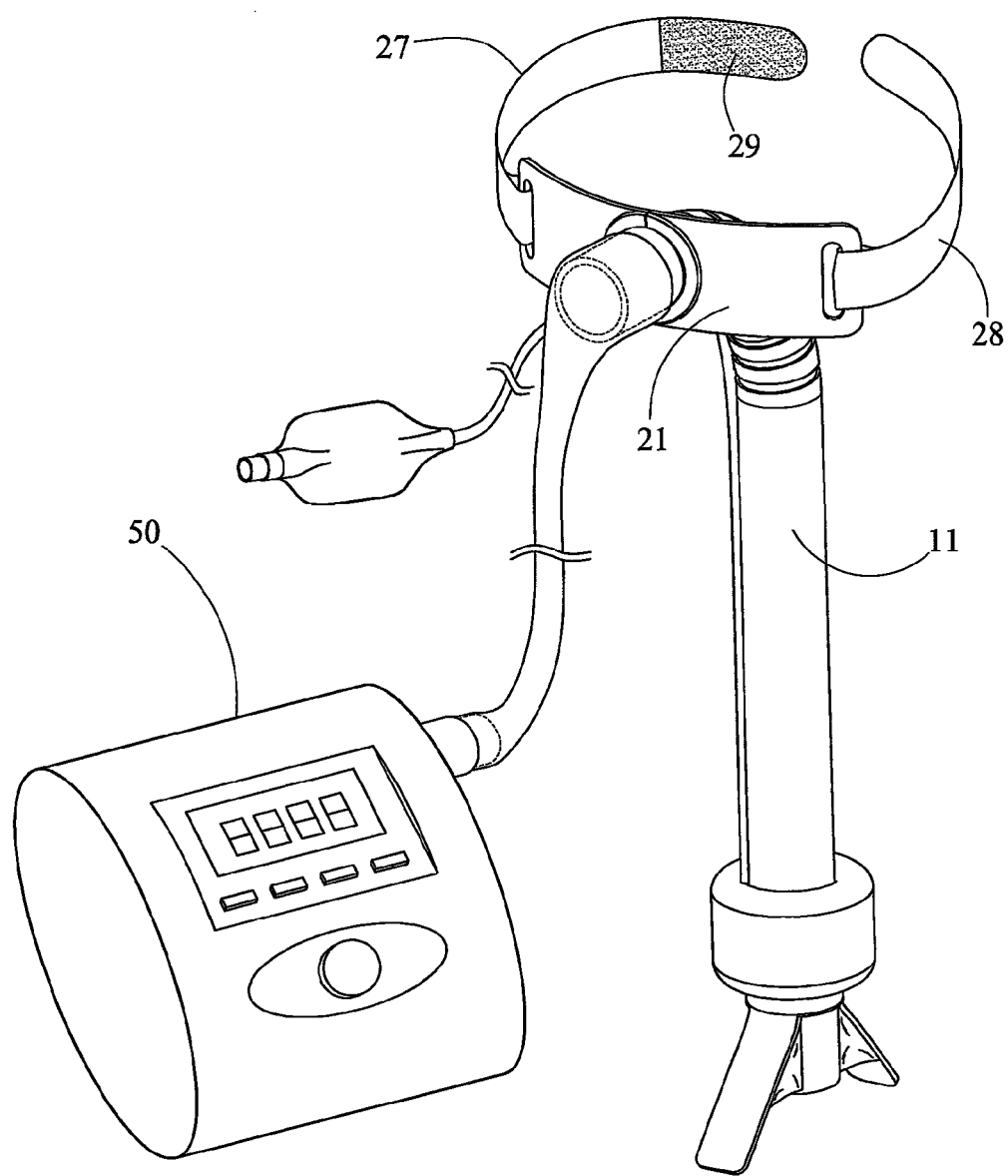
FIG. 1 is a perspective view of a tracheotomy tube set according to the invention.
Figure 2:
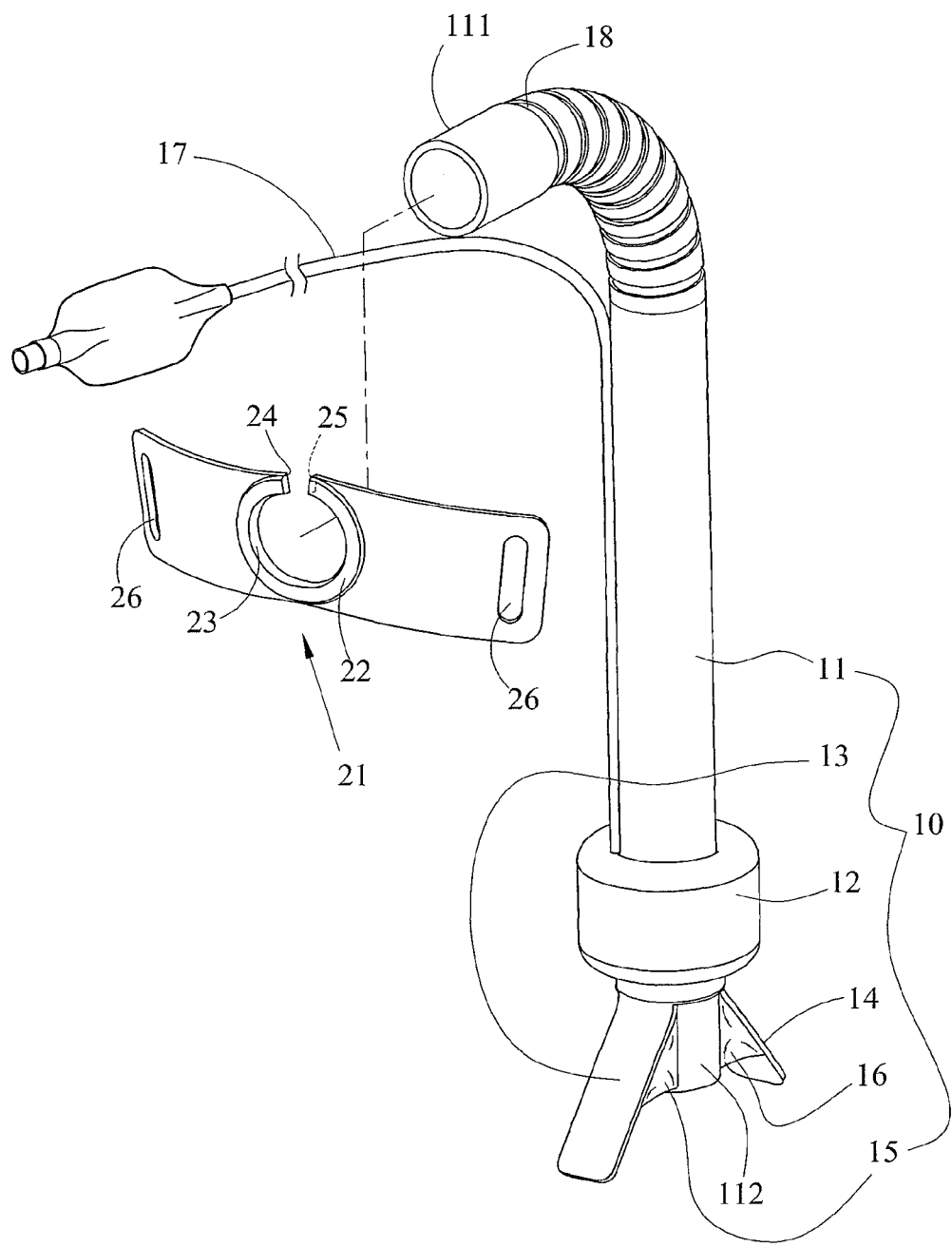
FIG. 2 is an exploded perspective view of the tracheotomy tube and the fixation device.

Referring to FIGS. 1 to 5, a tracheotomy tube set in accordance with the invention comprises the following components as discussed in detail below.

A tracheotomy tube 10 is hollow and formed integrally. The tracheotomy tube 10 comprises a cannula 11, a substantially cylindrical balloon cuff 12 formed proximal to a distal end of the cannula 11, a first wing 13 extending from one side of one end of the balloon cuff 12, a second wing 14 extending from the other side of one end of the balloon cuff 12, a first wedge balloon 15 formed between the first wing 13 and an insertion section 112 between the balloon cuff 12 and the distal end of the cannula 11, and a second wedge balloon 16, opposite to the first wedge balloon 15, formed between the second wing 14 and the insertion section 112.

The cannula 11 further comprises a connecting member 111 at a proximal end. A plastic line 17 is interconnected between both the first and second wedge balloons 15, 16 and an air source (not shown). A bellows member 18 is formed between the connecting member 111 and the main portion of the cannula 11.

A fixation device 21 is substantially rectangular and slightly curved. The fixation device 21 comprises a C-shaped flange 22, a hole 23 through the flange 22, a first snapping member 24 formed at one end of the flange 22, a second snapping member 25 formed at the other end of the flange 22, two slots 26 formed at both sides of the fixation device 21 respectively, a first strap 27 having one end looped around one slot 26 and secured thereto, a second strap 28 having one end looped around the other slot 26 and secured thereto, and a hook and loop fabric fastener 29 formed at the other end of the first strap 27 for looping around the neck of a patient and securing thereto.

The flange 22 can be tightly put on the connecting member 111 by inserting the connecting member 111 through the hole 23 and by then snapping the first and second snapping members 24 and 25 toward each other and urging against the bellows member 18. As a result, the fixation device 21 and the tracheotomy tube 10 are assembled. Further, the bellows member 18 allows the insertion of the tracheotomy tube 10 into the trachea 31 to be adjusted in order to fit different patients of various heights during a tracheotomy.

A physician may insert the cannula 11 into the trachea 31 through the larynx of a patient during a tracheotomy. Next, the physician may activate a controller to pump air from the air source into the first and second wedge balloons 15 and 16 for inflation. The inflated first and second wedge balloons 15 and 16 in turn pivotably push the first and second wings 13, 14 outward until being fastened at joining portions 33 of the primary bronchi 32 and the trachea 31 (see FIG. 4).

Figure 3:
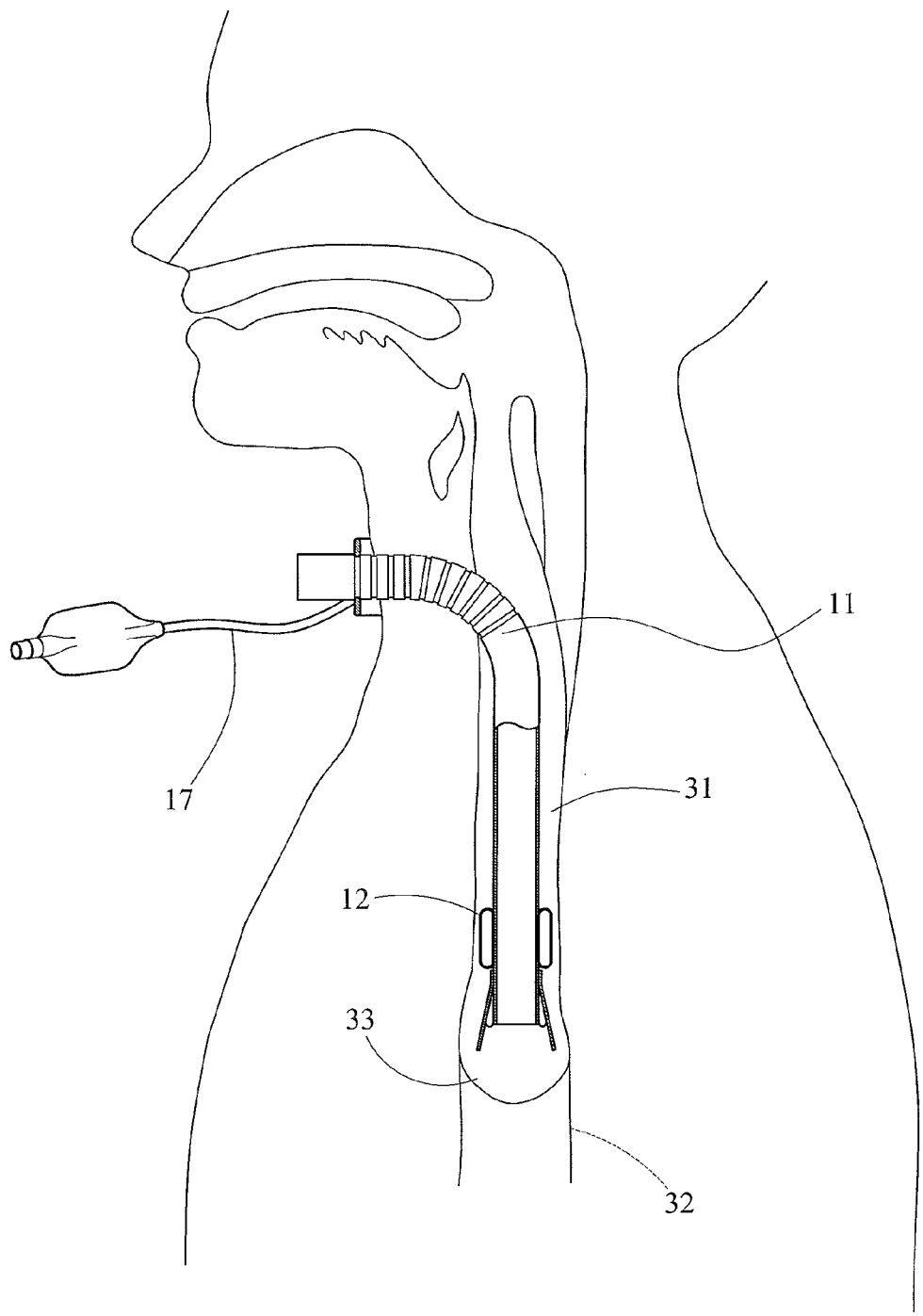
FIG. 3 is a schematic side elevation of the assembled tracheotomy tube and the fixation device with the tracheotomy tube inserted into the trachea of a patient, the first and second wedge balloons before inflating, and the balloon cuff before expanding being shown during a tracheotomy.
Figure 4:
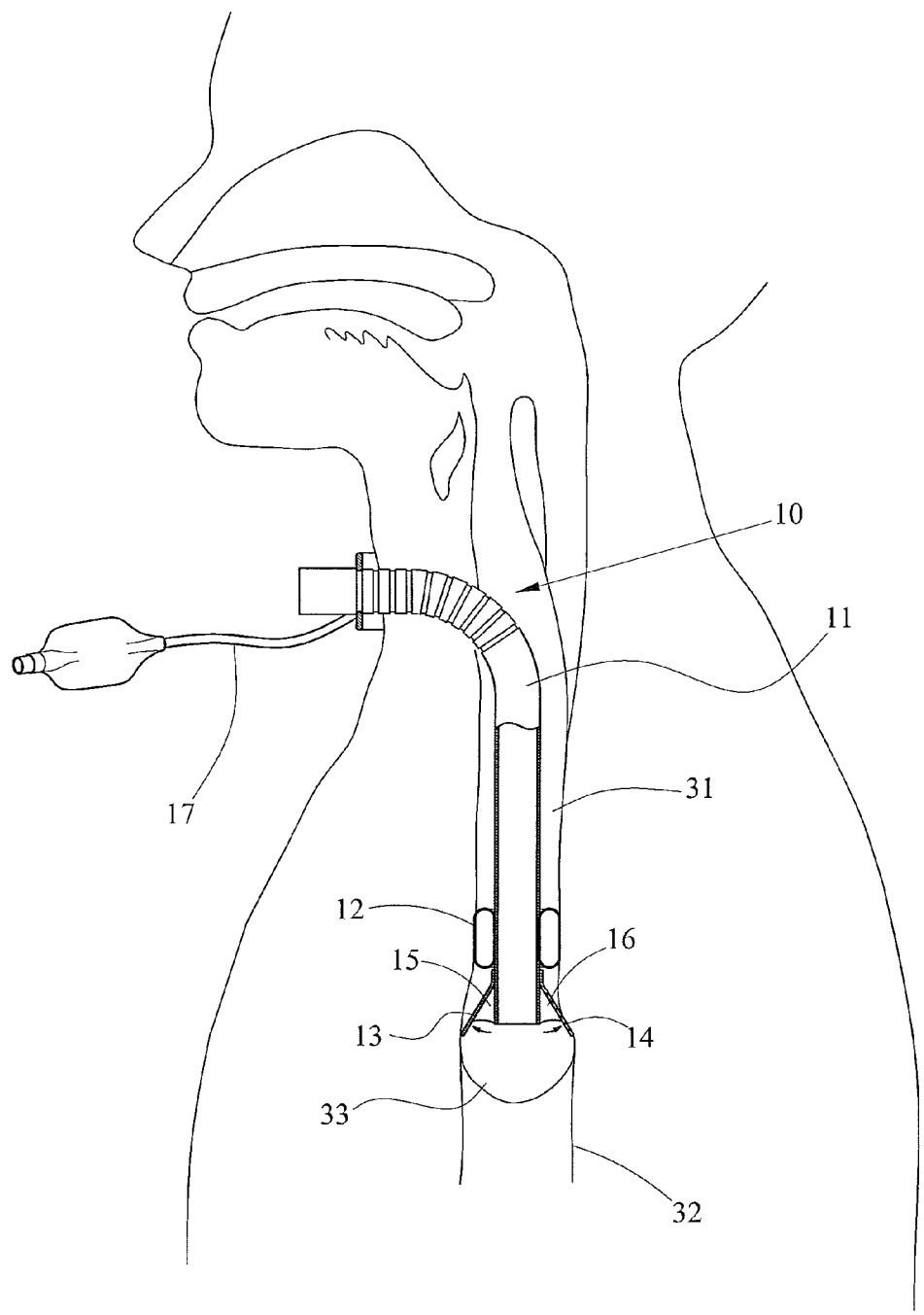
FIG. 4 is a view similar to FIG. 3 showing the first and balloon cuffs after inflating and the balloon cuff after expanding.
Figure 5:
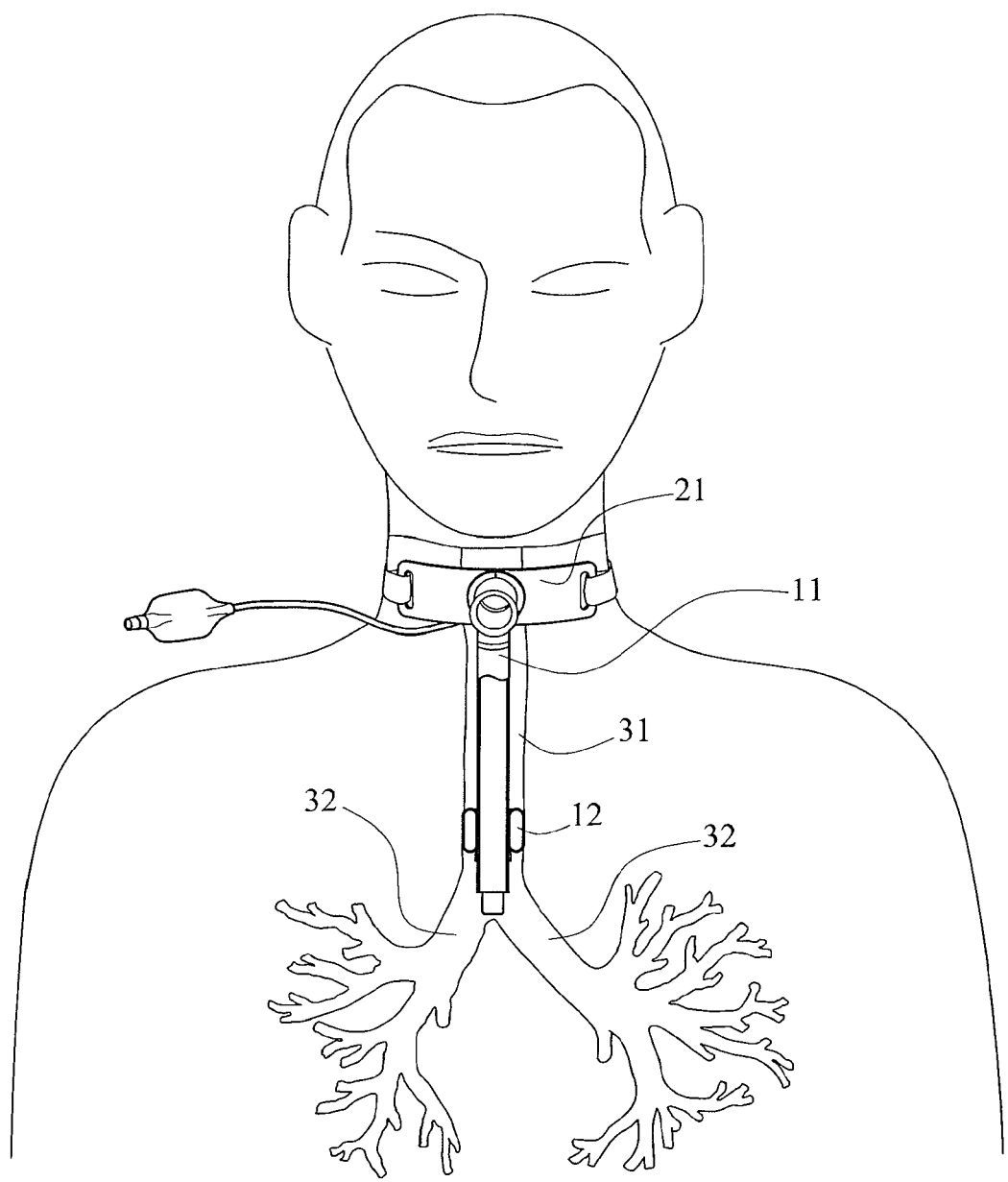
FIG. 5 is a front view of FIG. 4.

The balloon cuff 12 is enclosed by a resilient membrane (not shown) and has a diameter less than that of the trachea 31 (see FIG. 3). The membrane can be expanded by the balloon cuff 12 to urge against an inner wall of the trachea 31 during a tracheotomy. Thus, food or foreign objects can be prevented from entering the primary bronchi 32. Otherwise, the lungs may be infected by microorganisms entering through the larynx and the trachea 31.

The connecting member 111 of the cannula 11 is further connected to an oxygen tank 50, so that oxygen can be delivered to the patient during a tracheotomy.

While the invention has been described in terms of preferred embodiments, those skilled in the art will recognize that the invention can be practiced with modifications within the spirit and scope of the appended claims.

What is claimed is:

1. A tracheotomy tube set comprising:
   a hollow tracheotomy tube comprising a cannula including a connecting member at a proximal end and a bellows member joining to the connecting member, a balloon cuff formed proximal to a distal end of the cannula, a first wing extending from one side of one end of the balloon cuff, a second wing extending from another side of the one end of the balloon cuff, a first wedge balloon formed between the first wing and an insertion section between the balloon cuff and the distal end of the cannula, a second wedge balloon, opposite to the first wedge balloon, formed between the second wing and the insertion section, and a line having one end communicating with both the first and second wedge balloons; and
   a fixation device comprising a split flange, a hole through the split flange, and two slots formed at two sides of the fixation device respectively;
   wherein the cannula is adapted to be inserted into a trachea of a patient during a tracheotomy, air is pumped into both the first and second wedge balloons for inflation from the line, and the first and second wedge balloons when inflated pivotably push the first and second wings outward until adapted to be fastened at joining portions of a primary bronchi and the trachea.

2. The tracheotomy tube set of claim 1, wherein the tracheotomy tube is formed integrally.

3. The tracheotomy tube set of claim 1, wherein the split flange comprises first and second snapping members formed at first and second ends respectively, with the connecting member inserted through the hole, the first and second snapping members are snapped toward each other and urged against the bellows member.

4. The tracheotomy tube set of claim 1, wherein the balloon cuff is resilient and is adapted to expand to urge against an inner wall of the trachea.

5. The tracheotomy tube set of claim 1, wherein the connecting member is connected to an oxygen tank with oxygen delivered from the oxygen tank to the tracheotomy tube.

6. The tracheotomy tube set of claim 1, wherein the fixation device further comprises a first strap having one end looped around one of the two slots and secured thereto, a second strap having one end looped around another of the two slots and secured thereto, and a hook and loop fabric fastener formed at another end of the first strap and adapted to loop around a neck of the patient and securing thereto.

\* \* \* \* \*